US012342984B2

(12) United States Patent
Sakurada

(10) Patent No.: US 12,342,984 B2
(45) Date of Patent: Jul. 1, 2025

(54) OBJECTIVE OPTICAL SYSTEM, IMAGE PICKUP APPARATUS, AND ENDOSCOPE

(71) Applicant: OLYMPUS CORPORATION, Hachioji (JP)

(72) Inventor: Ippei Sakurada, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 531 days.

(21) Appl. No.: 17/887,356

(22) Filed: Aug. 12, 2022

(65) Prior Publication Data
US 2023/0055267 A1 Feb. 23, 2023

Related U.S. Application Data

(63) Continuation of application No. PCT/JP2020/008662, filed on Mar. 2, 2020.

(51) Int. Cl.
*A61B 1/00* (2006.01)
*G02B 3/04* (2006.01)
*G02B 23/24* (2006.01)

(52) U.S. Cl.
CPC ............ *A61B 1/00096* (2013.01); *G02B 3/04* (2013.01); *G02B 23/243* (2013.01)

(58) Field of Classification Search
CPC .. A61B 1/00096; A61B 1/00188; G02B 3/04; G02B 23/243
See application file for complete search history.

(56) References Cited

U.S. PATENT DOCUMENTS

| 8,284,501 | B2 | 10/2012 | Sudoh |
| 9,778,438 | B2 | 10/2017 | Sun |
| 2011/0043927 | A1 | 2/2011 | Sudoh |

(Continued)

FOREIGN PATENT DOCUMENTS

| EP | 2165640 A1 * | 3/2010 | ......... A61B 1/00177 |
| JP | 2000352665 A * | 12/2000 | |

(Continued)

OTHER PUBLICATIONS

International Preliminary Report on Patentability (IPRP) (and English language translation thereof) dated Sep. 15, 2022 issued in counterpart International Application No. PCT/JP2020/008662.

(Continued)

*Primary Examiner* — Stephone B Allen
(74) *Attorney, Agent, or Firm* — Holtz, Holtz & Volek PC

(57) ABSTRACT

There is provided an objective optical system, an image pickup apparatus, and an endoscope that are short in overall length and simple in structure and have a focusing function. The objective optical system includes, in order from the object side to the image side, a positive front lens group and a positive rear lens group. Focusing is performed by moving the front lens group along the optical axis. The front lens group includes, in order from the object side, a negative first lens, a positive second lens, an aperture stop, and a positive third lens, as lenses having refractive power. The rear lens group includes, in order from the object side, a positive cemented fourth lens and a positive fifth lens having a convex surface facing toward the object. The objective optical system satisfies the following conditional expression (1):

$$0.35 < FL/Ff < 0.85 \qquad (1).$$

12 Claims, 14 Drawing Sheets

(56) References Cited

U.S. PATENT DOCUMENTS

| | | | |
|---|---|---|---|
| 2015/0309289 A1* | 10/2015 | Nakamura | ......... A61B 1/00096 |
| | | | 359/740 |
| 2016/0356986 A1 | 12/2016 | Sun | |
| 2018/0364452 A1* | 12/2018 | Usui | ..................... G02B 13/18 |

FOREIGN PATENT DOCUMENTS

| | | | |
|---|---|---|---|
| JP | 2004020972 A | | 1/2004 |
| JP | 2006003549 A | | 1/2006 |
| JP | 2009104082 A | | 5/2009 |
| JP | 2011013582 A | | 1/2011 |
| JP | 2013232014 A | | 11/2013 |
| JP | 2014174234 A | | 9/2014 |
| JP | 2017003678 A | | 1/2017 |
| JP | 2018185383 A | * | 11/2018 |

OTHER PUBLICATIONS

International Search Report (ISR) (and English translation thereof) dated May 26, 2020, issued in International Application No. PCT/JP2020/008662.

Written Opinion dated May 26, 2020, issued in International Application No. PCT/JP2020/008662.

* cited by examiner

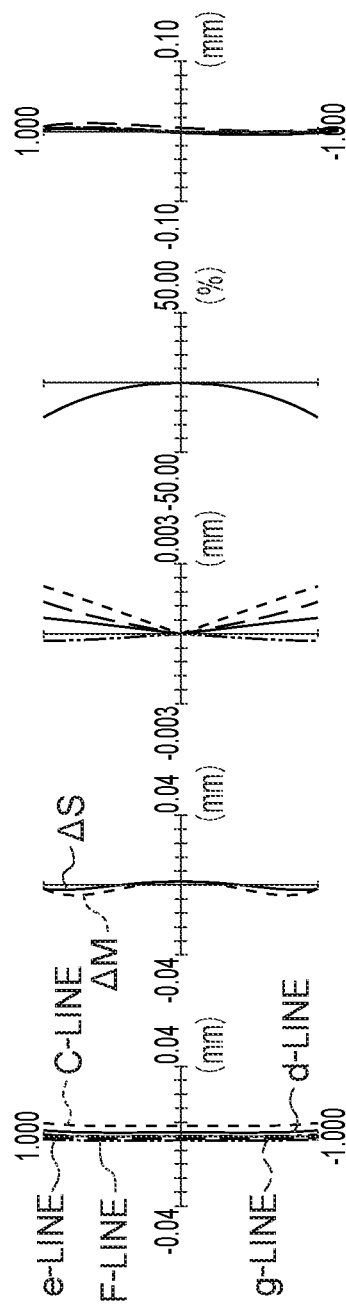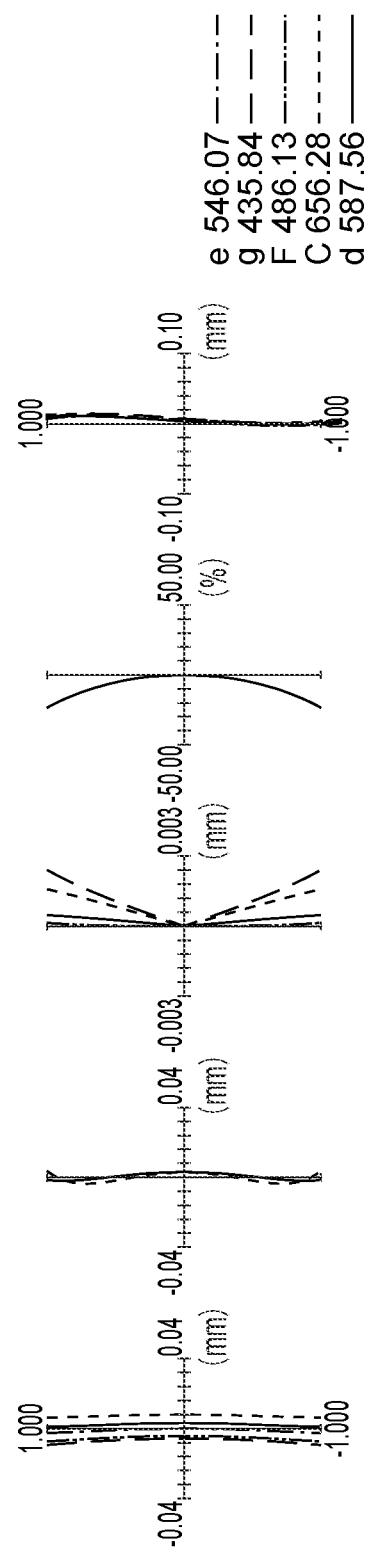

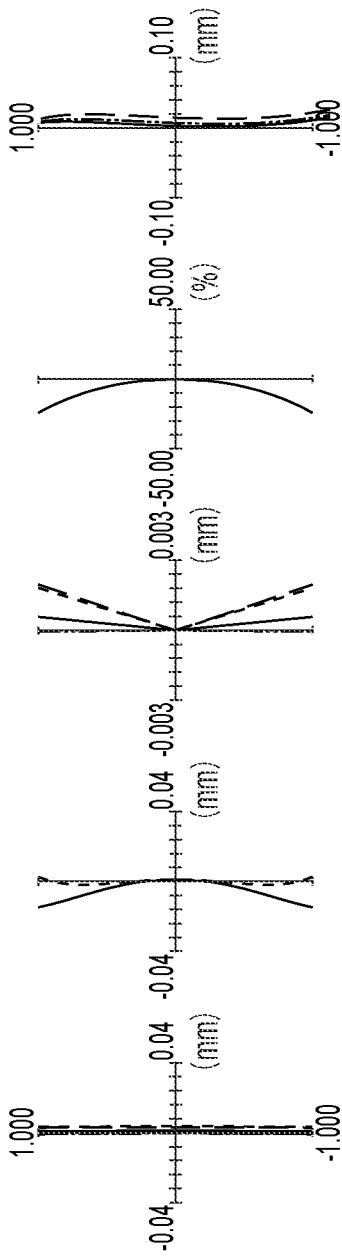
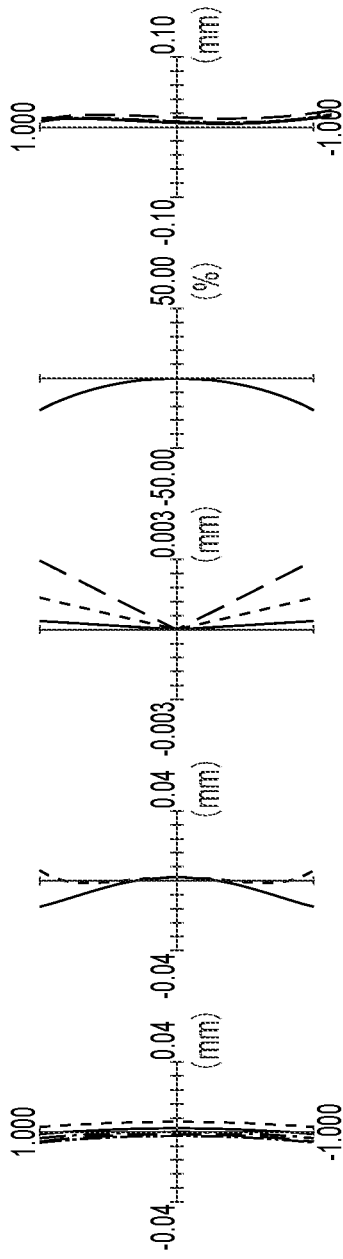

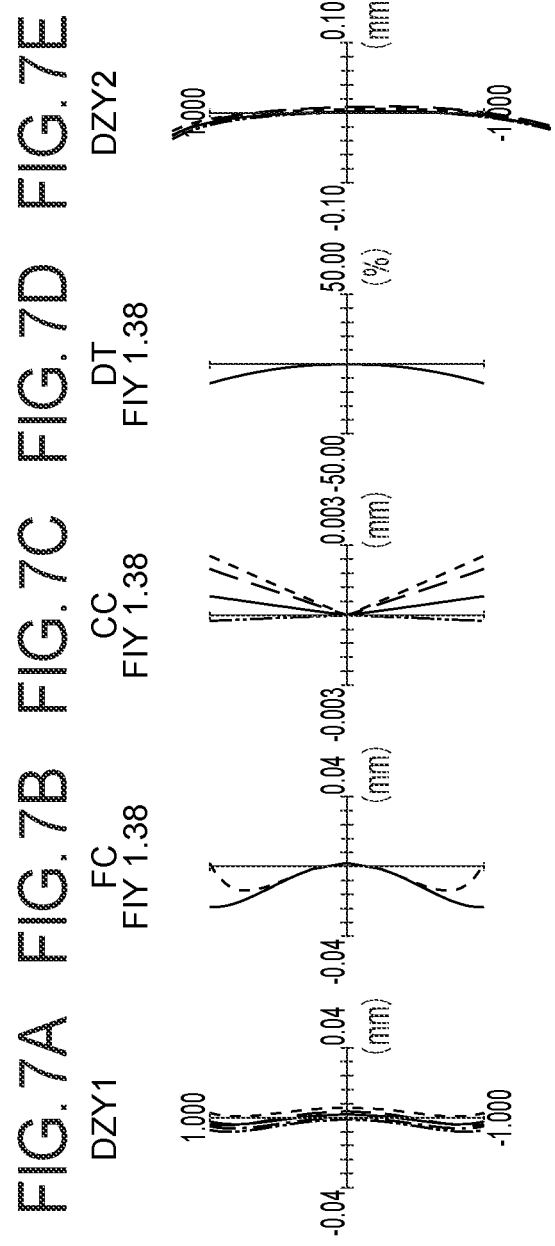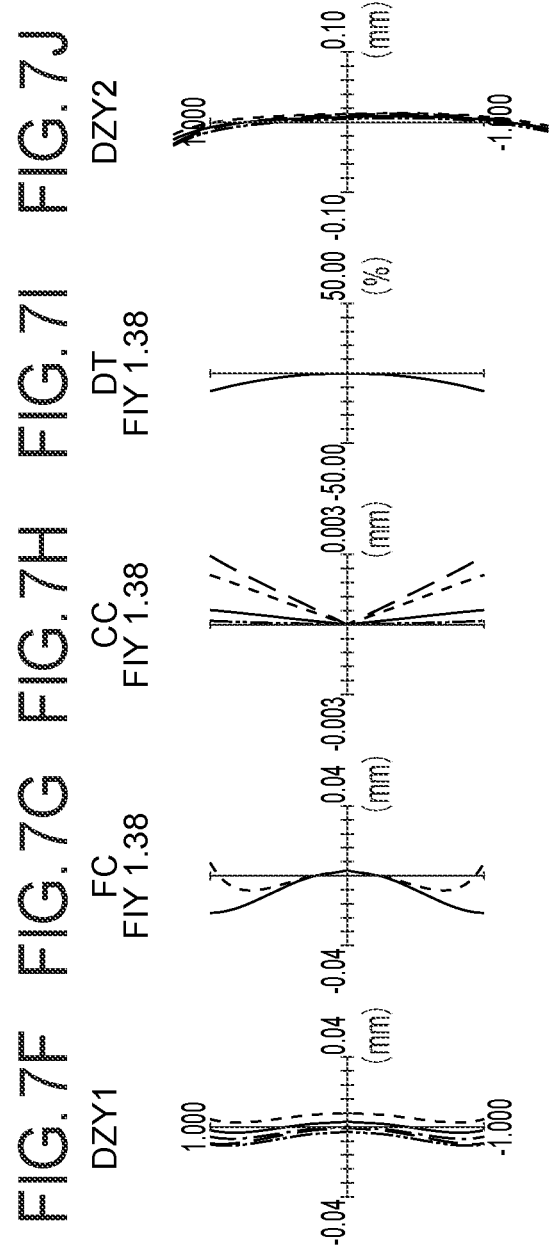

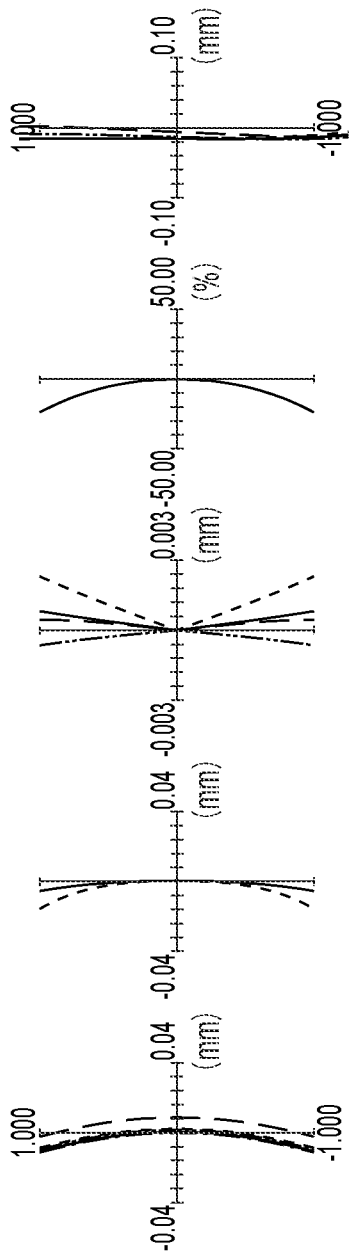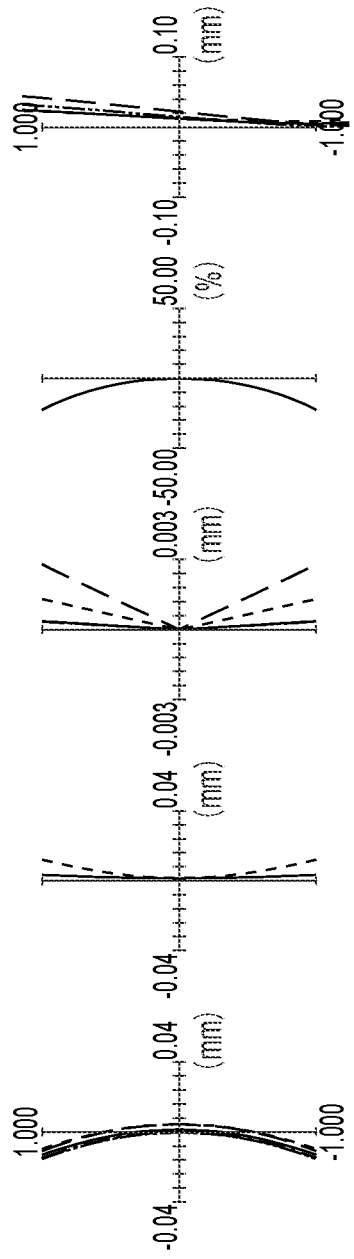

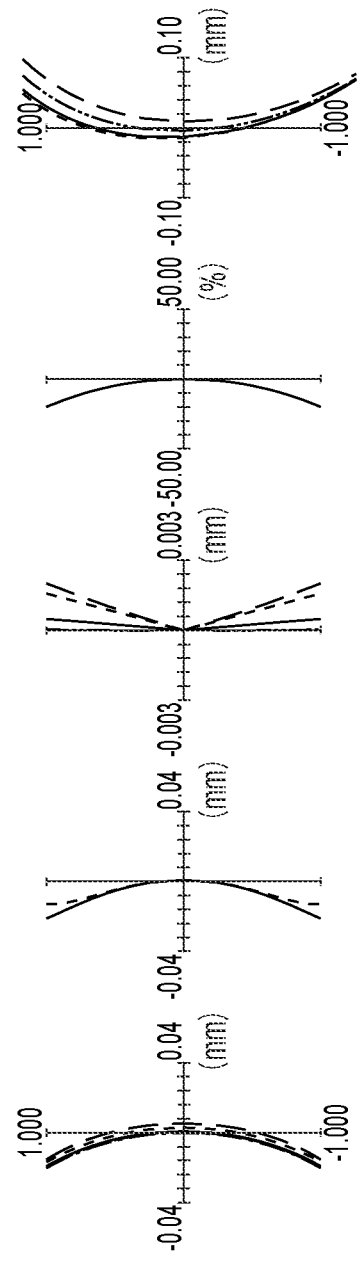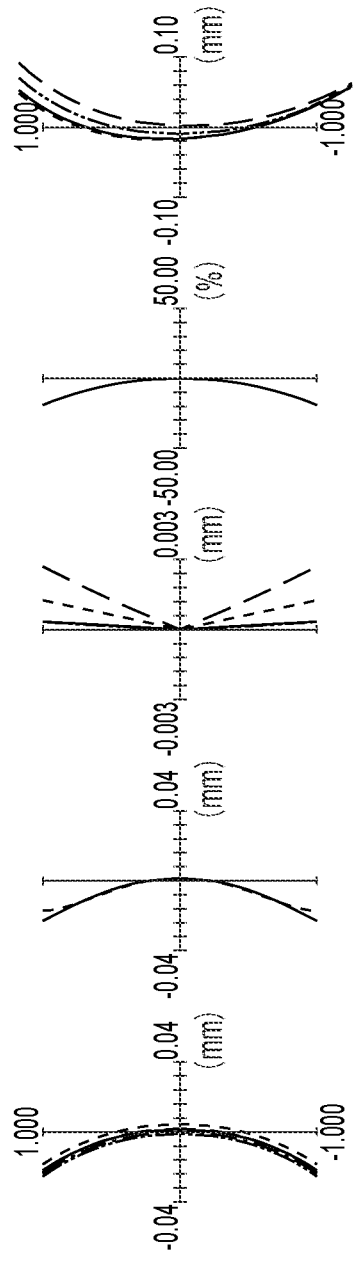

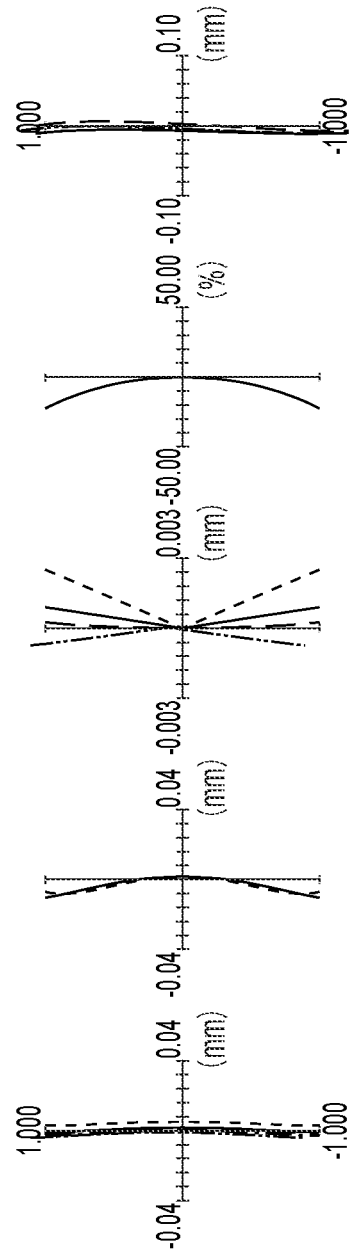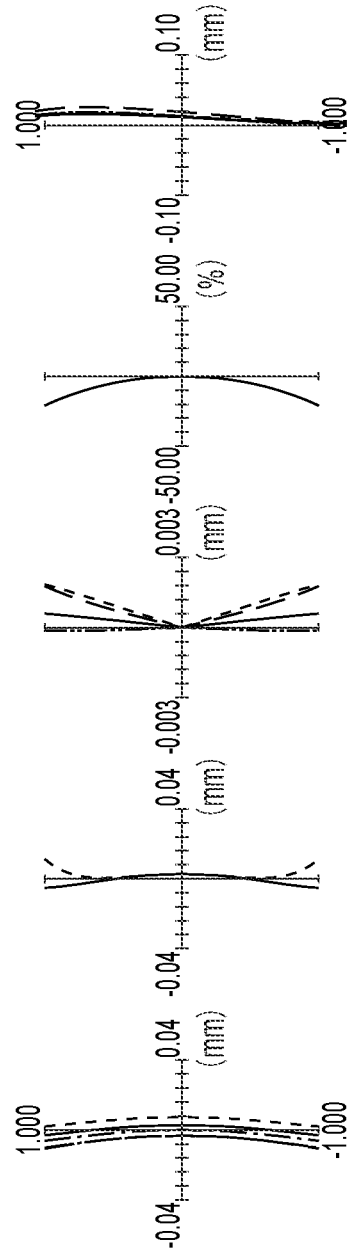

OBJECTIVE OPTICAL SYSTEM, IMAGE PICKUP APPARATUS, AND ENDOSCOPE

CROSS REFERENCES

The present application is a continuation application of PCT/JP2020/008662 filed on Mar. 2, 2020; the entire contents of which are incorporated herein by reference.

BACKGROUND OF INVENTION

Technical Field

The present invention relates to an objective optical system, an image pickup apparatus, and an endoscope.

Description of the Related Art

With reduction in size of the pixels of imagers, the number of pixels of endoscopic images has been increasing in the field of technology relating to endoscopes. Increases in the number of pixels of endoscopic images improve the visibility of blood vessels and nerves and help precise anatomic understanding, thereby enabling safe and efficient diagnosis and treatment.

Objective optical systems used in endoscopes are designed to have a large depth of field. The depth of field is the range in the object field in which sharp object images can be obtained. In other words, the depth of field represents the area in front of and behind an object on which the optical system is focused in which objects appear to be in focus or sharp to the viewer. The depth of field is represented by the imaging distance (i.e. the distance between the object and the imaging system).

Reduction in the pixel size invites the problem of decreased depth of field. To control decrease in the depth of field, focus switching is employed to achieve a sufficiently large depth of field.

However, providing a mechanism for focus switching in an objective optical system leads to increase in the overall length of the optical system and complexity in structure.

Japanese Patent Application Laid-Open No. 2009-104082 discloses an optical system composed of two lens groups having a positive refractive.

SUMMARY

An objective optical system according to at least some embodiments of the present invention comprises, in order from the object side to the image side:
  a positive front lens group; and
  a positive rear lens group,
  wherein focusing is performed by moving the front lens group along the optical axis,
  the front lens group includes, in order from the object side, a negative first lens, a positive second lens, an aperture stop, and a positive third lens, as lenses having refractive power,
  the rear lens group includes, in order from the object side, a positive cemented fourth lens and a positive fifth lens having a convex surface facing toward the object, and
  the objective optical system satisfies the following conditional expression (1):

$$0.35 < FL/Ff < 0.85 \tag{1}$$

where Ff is the focal length of the front lens group, and FL is the focal length of the entire objective optical system in a normal observation state.

There is also provided an image pickup apparatus. An image pickup apparatus according to at least some embodiments of the present invention comprises an objective optical system and an imager, wherein the objective optical system includes, in order from the object side to the image side, a positive front lens group and a positive rear lens group, focusing is performed by moving the front lens group along the optical axis, and the objective optical system is the above-described objective optical system.

There is also provided an endoscope. An endoscope according to at least some embodiments of the present invention comprises an objective optical system and an imager, wherein the objective optical system includes, in order from the object side to the image side, a positive front lens group and a positive rear lens group, focusing is performed by moving the front lens group along the optical axis, and the objective optical system is the above-described objective optical system.

BRIEF DESCRIPTION OF THE DRAWINGS

FIGS. 3A, 3B, 3C, 3D, 3E, 3F, 3G, 3H, 3I, and 3J are diagrams showing aberrations of the objective optical system of example 1;

FIGS. 5A, 5B, 5C, 5D, 5E, 5F, 5G, 5H, 5I, and 5J are diagrams showing aberrations of the objective optical system of example 2;

FIGS. 7A, 7B, 7C, 7D, 7E, 7F, 7G, 7H, 7I, and 7J are diagrams showing aberrations of the objective optical system of example 3;

FIGS. 9A, 9B, 9C, 9D, 9E, 9F, 9G, 9H, 9I, and 9J are diagrams showing aberrations of the objective optical system of example 4;

FIGS. 11A, 11B, 11C, 11D, 11E, 11F, 11G, 11H, 11I, and 11 are diagrams showing aberrations of the objective optical system of example 5;

FIGS. 13A, 13B, 13C, 13D, 13E, 13F, 13G, 13H, 13I, and 13J are diagrams showing aberrations of the objective optical system of example 6;

DETAILED DESCRIPTION

Prior to description of examples of the present invention, the operation and advantageous effects of embodiments according to certain modes of the present invention will be described. To describe the operation and advantageous effects of the embodiments specifically, specific exemplary modes will be given. However, the exemplary modes and examples that will be described later constitute only a portion of the modes encompassed by the present invention, which include many variations. Therefore, it should be understood that the present invention is not limited by the exemplary modes.

In the following, embodiments of the objective optical system, the image pickup apparatus, and the endoscope will be described with reference to the drawings. Specifically, the structures of the embodiments, the reason why such structures are employed, and the operations of the embodiments will be described. It should be understood that the present invention is not limited by the embodiments.

First Embodiment

Figure 1:
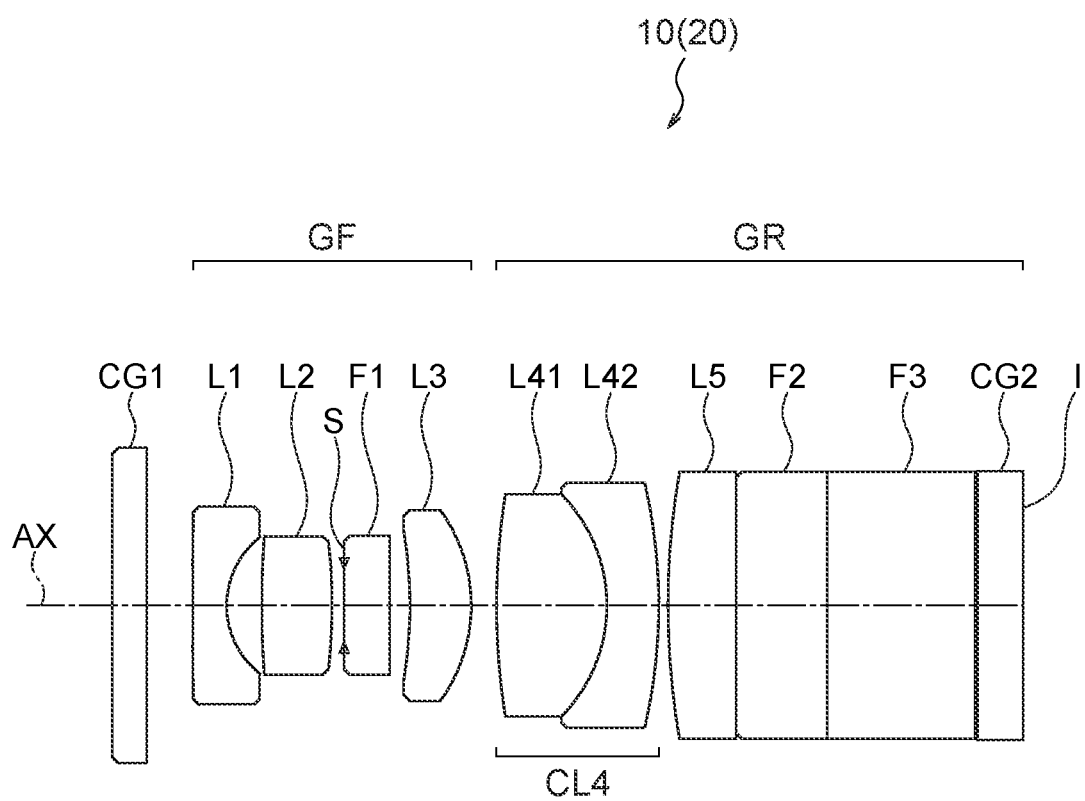
FIG. 1 is a cross sectional view of the lenses in objective optical systems according to first and second embodiments.

FIG. 1 is a cross sectional view of the lenses in an objective optical system 10 according to a first embodiment.

The objective optical system includes, in order from the object side to the image side, a positive front lens group GF and a positive rear lens group GR. Focusing is performed by moving the front lens group GF along the optical axis. The objective optical system 10 satisfies the following conditional expression (1):

$$0.35 < FL/Ff < 0.85 \quad (1)$$

where Ff is the focal length of the front lens group GF, and FL is the focal length of the entire objective optical system 10 in a normal observation state.

Conditional expression (1) defines an appropriate range of the ratio of the focal length of the front lens group GF and the focal length of the entire objective optical system 10.

If the value of FL/Ff falls below the lower limit value of conditional expression (1), the amount of shift of the front lens group GF required for focusing will be large. This makes the entire length of the objective optical system 10 long. Increase in the amount of shift of the front lens group GF leads to increase in the ray height of the front lens group GF and makes off-axial spherical aberration worse. Moreover, the variation in astigmatism with focusing increases, and the optical performance is deteriorated.

If the value of FL/Ff exceeds the upper limit value of conditional expression (1), the amount of shift of the front lens group GF required for focusing is very small. This makes it difficult to control driving of the focusing group. Moreover, the refractive power of the front lens group GF is so large as to make axial spherical aberration and off-axial spherical aberration worse. Astigmatism cannot be corrected satisfactorily. The Petzval sum will be made worse due to inappropriate refractive power arrangement.

As above, according to the first embodiment, there is provided an objective optical system that is short in overall length and simple in structure and has a focusing function.

It is preferred that the following conditional expression (1') be satisfied instead of conditional expression (1):

$$0.45 < FL/Ff < 0.66 \quad (1').$$

It is more preferred that the following conditional expression (1") be satisfied instead of conditional expression (1):

$$0.57 < FL/Ff < 0.66 \quad (1'').$$

Second Embodiment

FIG. 1 is a cross sectional view of the lenses in an objective optical system 20 according a second embodiment. The configuration of the lenses in the objective optical system is the same as that of the objective optical system 10 according to the first embodiment.

The objective optical system 20 according to the second embodiment includes, in order from the object side to the image side, and a positive front lens group GF and a positive rear lens group GR. Focusing is performed by moving the front lens group GF along the optical axis AX. The objective optical system 20 satisfies the following conditional expression (4):

$$0.12 < (1-\beta^2) \times \gamma^2 < 0.71 \quad (4)$$

where $\beta$ is the imaging magnification of the front lens group GF in the normal observation state, and $\gamma$ is the imaging magnification of the rear lens group GR in the normal observation state.

Conditional expression (4) defines an appropriate relationship between the imaging magnification of the front lens group GF and the imaging magnification of the rear lens group GR.

If the value of $(1-\beta^2) \times \gamma^2$ falls below the lower limit value of conditional expression (4), the amount of shift of the front lens group GF required for focusing is large. This makes the entire length of the objective optical system 20 long. Increase in the amount of shift of the front lens group GF leads to increase in the ray height of the front lens group GF and makes off-axial spherical aberration worse. Moreover, the variation in astigmatism with focusing increases, and the optical performance is deteriorated.

If the value of $(1-\beta^2) \times \gamma^2$ exceeds the upper limit value of conditional expression (4), the amount of shift of the front lens group GF required for focusing is very small. This makes it difficult to control driving of the focusing group. Moreover, the refractive power of the front lens group GF is so large as to make axial spherical aberration and off-axial spherical aberration worse. Astigmatism cannot be corrected satisfactorily. The Petzval sum will be made worse due to inappropriate refractive power arrangement.

As above, according to the second embodiment, there is provided an objective optical system that is short in overall length and simple in structure and has a focusing function.

It is preferred that the following conditional expression (4') be satisfied instead of conditional expression (4):

$$0.20 < (1-\beta^2) \times \gamma^2 < 0.43 \quad (4').$$

It is more preferred that the following conditional expression (4") be satisfied instead of conditional expression (4"):

$$0.32 < (1-\beta 2) \times \gamma^2 < 0.43 \quad (4'').$$

In a preferred mode of the first or the second embodiment, the objective optical system 10, 20 have a cover glass CG1 disposed closest to the object.

The objective optical system 10, 20 has a cover glass CG1. For example, the cover glass CG1 is attached to a lens frame by soldering. Thus, air-tightness is established, and the objective system 10, 20 can satisfactorily endure disinfection or sterilization treatment applied to it. Hence, the objective optical system 10, 20 is suitable for use in a rigid endoscope. An example of the material of the cover glass CG1 is sapphire. Sapphire has excellent temperature characteristics and a high degree of hardness, and the cover glass CG1 can be prevented from deforming through temperature changes during soldering or being scratched by collision with something.

In a preferred mode of the first or the second embodiment, it is desirable that the front lens group GF include a negative first lens L1 disposed closest to the object, a positive third lens L3, and an aperture stop S.

With this configuration, it is possible to achieve an appropriate angle of view by the negative first lens L1 at the front end and correct spherical aberration and the Petzval sum by the third lens L3.

In a preferred mode of the first or the second embodiment, it is desirable that the front lens group GF include, in order from the object side, a negative first lens L1, a positive second lens L2, an aperture stop S, and a positive third lens L3 as lenses having refractive power. It is also desirable that the rear lens group GR include, in order from the object side, a positive cemented fourth lens CL4, and a positive fifth lens L5 having a convex surface facing toward the object side.

Among the lenses in the front lens group GF, the negative first lens L1 disposed closest to the object provides a sufficiently large angle of view in the range of 80° to 90°. The positive second lens L2 contributes to correction of coma and the Petzval sum. The positive third lens L3 contributes to correction of spherical aberration generated by the negative first lens L1 and the Petzval sum.

Among the lenses in the rear lens group GR, the positive cemented forth lens CL4 corrects chromatic aberration. The positive fifth lens L5 reduces the magnification of the rear lens group GR and the focus sensitivity.

In a preferred mode of the first or the second embodiment, it is desirable that the following conditional expression (2) be satisfied:

$$-0.43<(r1i \times r3i)/Ff^2<-0.05 \quad (2)$$

where r1$i$ is the curvature radius of the image side surface of the negative first lens L1, r3$i$ is the curvature radius of the image side surface of the positive third lens L3, and Ff is the focal length of the front lens group GF.

If conditional expression (2) is not satisfied, a symmetric lens configuration with respect to the aperture stop S is not achieved. Then, it is difficult to correct spherical aberration and the Petzval sum while keeping appropriate focus sensitivity.

In a preferred mode of the first or the second embodiment, it is desirable that the following conditional expression (3) be satisfied:

$$-0.57<(r4c \times r5o)/Fr^2<-0.13 \quad (3)$$

where r4$c$ is the curvature radius of the cemented surface of the positive cemented fourth lens CL4, r5$o$ is the curvature radius of the object side surface of the positive fifth lens L5, and Fr is the focal length of the rear lens group GR.

If conditional expression (3) is not satisfied, it is difficult to correct coma, axial chromatic aberration, and chromatic aberration of magnification while keeping appropriate focus sensitivity.

In a preferred mode of the first or the second embodiment, it is desirable that the first lens L1 be a negative bi-aspheric meniscus lens having a convex surface facing toward the object side, the second lens L2 be a positive meniscus lens having a convex surface facing toward the object side, and the third lens L3 be a positive lens whose image side surface is an aspheric surface.

In the case where the objective optical system is used in a stereoscopic endoscope, the above configuration is preferable if satisfactory correction of distortion is required. The first lens L1 can correct distortion excellently. The second lens L2 allows a symmetric lens configuration with respect to the aperture stop S. Hence, it is possible to correct distortion excellently. The third lens L3 can excellently correct spherical aberration and coma generated in the region on the object side of the third lens L3.

Third Embodiment

Figure 14:
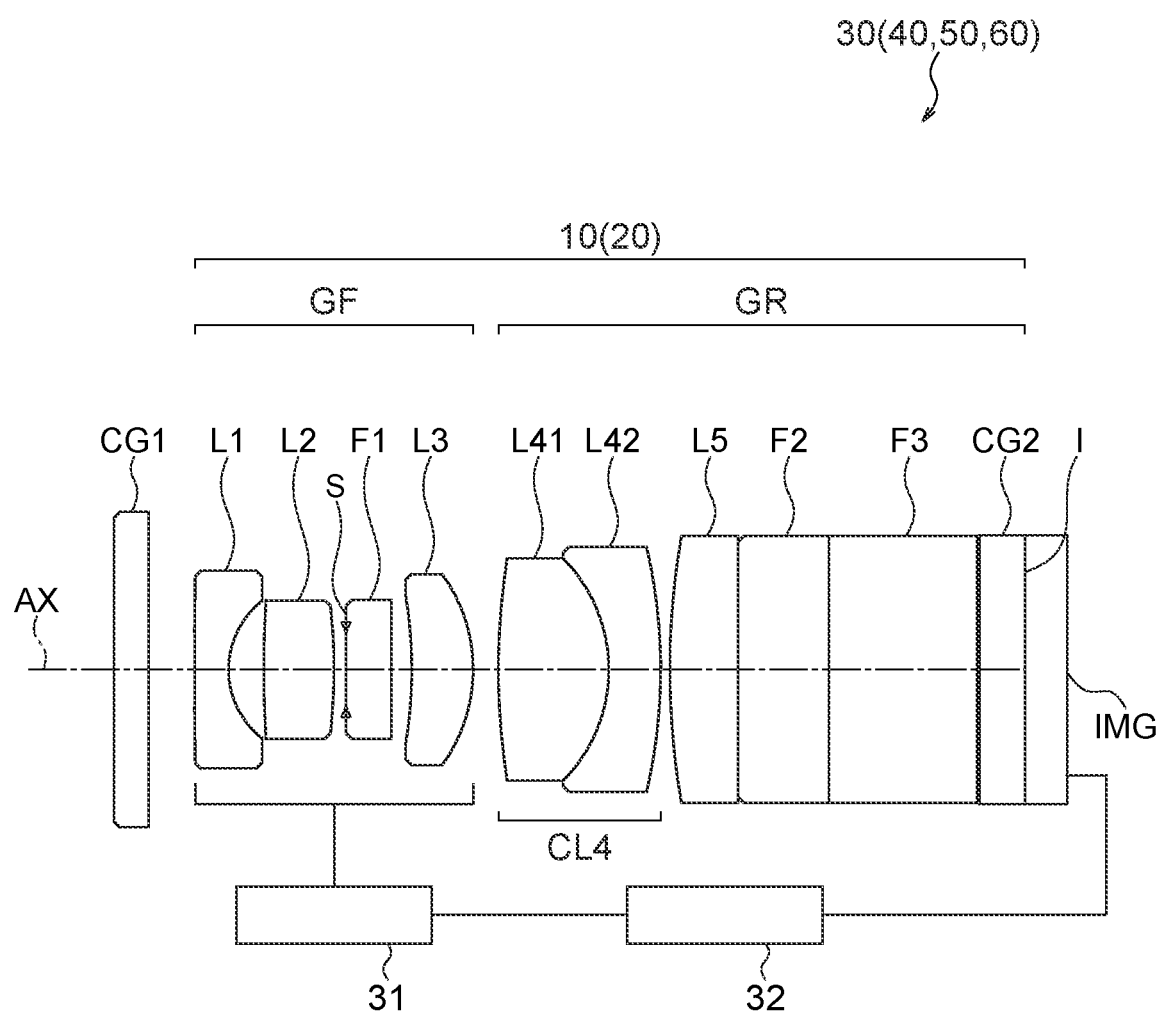
FIG. 14 is a diagram showing an image pickup apparatus according to a third embodiment, an image pickup apparatus according to a fourth embodiment, an endoscope according to a fifth embodiment, and an endoscope according to a sixth embodiment.

FIG. 14 is a diagram showing an image pickup apparatus 30 according to a third embodiment. The configuration of the lenses is the same as that of the objective optical system 10 according to the first embodiment.

The image pickup apparatus 30 according to the third embodiment includes an objective optical system 10 and an imager IMG.

The objective optical system 10 includes, in order from the object side to the image side, a positive front lens group GF and a positive rear lens group GR. Focusing is performed by moving the front lens group GF along the optical axis AX. The objective optical system used in this image pickup apparatus 30 is the objective optical system 10 according to the first embodiment.

The image pickup apparatus 30 has a lens driver 31 including a motor and an actuator. The lens driver 31 moves the front lens group GF along the optical axis AX. Focusing is performed by moving the front lens group GF. The image pickup apparatus 30 has a processor 32, which controls the lens driver 31 and performs signal processing on signals output from the imager IMG.

As above, according to the third embodiment, there is provided an image pickup apparatus including an optical system that is short in overall length and simple in structure and has a focusing function.

Fourth Embodiment

FIG. 14 is a diagram showing an image pickup apparatus 40 according to a fourth embodiment. The configuration of the lenses is the same as that of the objective optical system 10 according to the first embodiment.

The image pickup apparatus 40 according to the fourth embodiment includes an objective optical system 20 and an imager IMG.

The objective optical system 20 includes, in order from the object side, a positive front lens group GF and a positive rear lens group GR. Focusing is performed by moving the front lens group GF along the optical axis AX. The objective optical system used in this image pickup apparatus 40 is the objective optical system 20 according to the second embodiment.

In a preferred mode of the third or the fourth embodiment, it is desirable that the image pickup apparatus 30, 40 include a cover glass CG1 disposed closest to the object.

As above, according to the fourth embodiment, there is provided an image pickup apparatus including an optical system that is short in overall length and simple in structure and has a focusing function.

Fifth Embodiment

FIG. 14 is a diagram showing an endoscope 50 according to a fifth embodiment. The configuration of the lenses is the same as that of the objective optical system 10 according to the first embodiment.

The endoscope 50 according to the fifth embodiment includes an objective optical system 10 and an imager IMG.

The objective optical system 10 includes, in order from the object side to the image side, a positive front lens group GF and a positive rear lens group GR. Focusing is performed by moving the front lens group GF along the optical axis AX. The objective optical system used in this endoscope 50 is the objective optical system 10 according to the first embodiment.

The endoscope 50 has a lens driver 31 including a motor and an actuator. The lens driver 31 moves the front lens group GF along the optical axis AX. Focusing is performed by moving the front lens group GF. The endoscope 50 has a processor 32, which controls the lens driver 31 and performs signal processing on signals output from the imager IMG.

As above, according to the fifth embodiment, there is provided an endoscope including an optical system that is short in overall length and simple in structure and has a focusing function.

Sixth Embodiment

FIG. 14 is a diagram showing an endoscope 60 according to a sixth embodiment. The configuration of the lenses is the same as that of the objective optical system 20 according to the second embodiment.

The endoscope 60 according to the sixth embodiment includes an objective optical system 20 and an imager IMG.

The objective optical system 20 includes, in order from the object side, a positive front lens group GF and a positive rear lens group GR. Focusing is performed by moving the front lens group GF along the optical axis AX. The objective optical system used in this endoscope 60 is the objective optical system 20 according to the second embodiment.

In a preferred mode of the fifth or the sixth embodiment, it is desirable that the endoscope 60 include a cover glass CG1 disposed closest to the object.

As above, according to the sixth embodiment, there is provided an endoscope including an optical system that is short in overall length and simple in structure and has a focusing function.

Example 1

An objective optical system of example 1 will be described.

Figure 2:
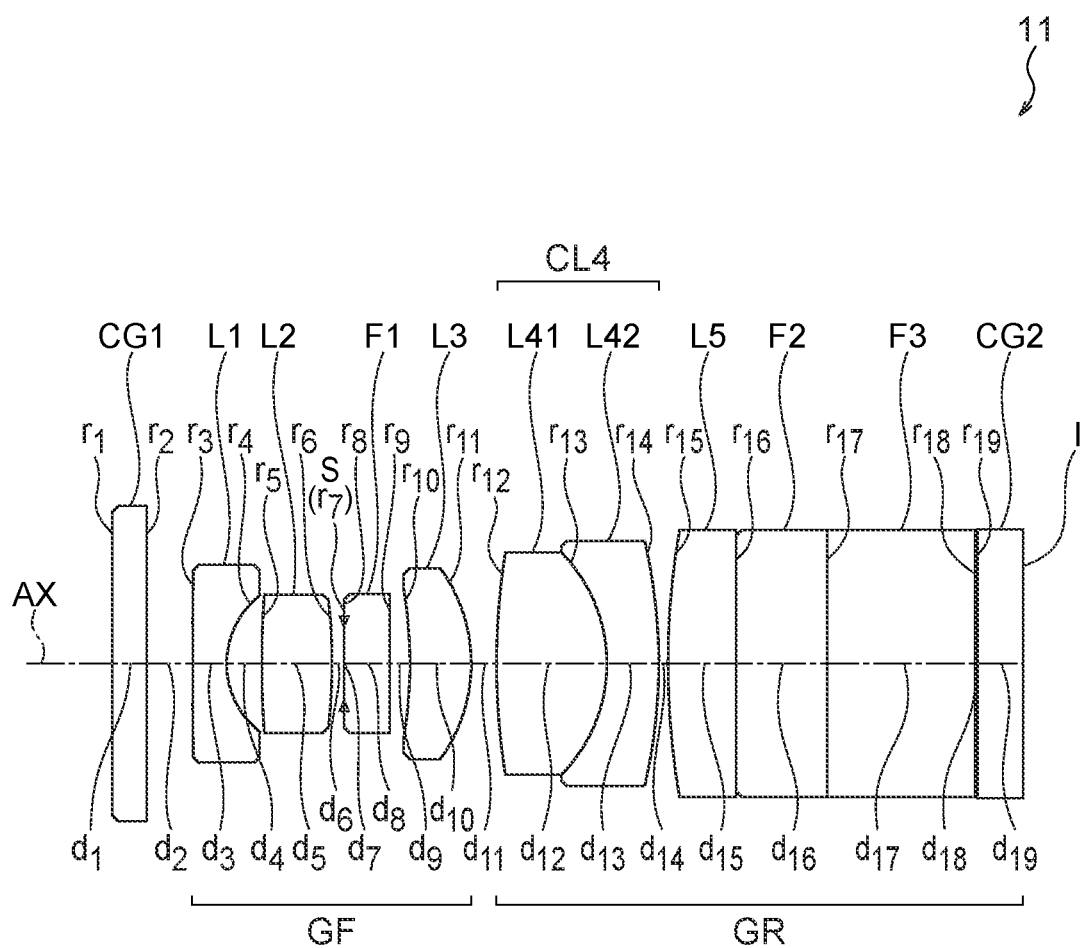
FIG. 2 is a cross sectional view of the lenses in an objective optical system of example 1.

FIG. 2 is a cross sectional view of the lenses in the objective optical system 11 of example 1 in a normal observation state.

The objective optical system 11 includes, in order from the object side to the image side, a positive front lens group GF and a positive rear lens group GR. The objective optical system 11 includes a cover glass CG1 disposed closest to the object.

The front lens group GF is moved along the optical axis AX to perform focusing, namely switching between the normal observation state (or far point observation state) and a short-distance observation state (or near point observation state). What is denoted by I in FIG. 2 is the image plane or the image pickup surface. The normal observation state is a state for observing a far point. The short-distance observation state is a state for observing a near point.

The front lens group GF includes, in order from the object side, a negative meniscus first lens L1 having a convex surface facing toward the object side, a positive biconvex second lens L2, an aperture stop S, a first plane parallel plate F1, and a positive meniscus third lens L3 having a convex surface facing toward the image side, as lenses having refractive power.

The rear lens group GR includes, in order from the object side, a positive biconvex lens L41, a negative meniscus lens L42 having a convex surface facing toward the image side, a positive planoconvex fifth lens L5 having a convex surface facing toward the object side, a second plane parallel plate F2, a third plane parallel plate F3, and a cover glass CG2. The positive lens L41 and the negative meniscus lens L42 are cemented together to constitute a positive cemented fourth lens CL4. The positive fifth lens L5, the second plane parallel plate F2, the third plane parallel plate F3, and the cover glass CG2 are cemented together. There is an adhesive layer between the third plane parallel plate F3 and the cover glass CG2.

The first to third plane parallel plates F1, F2, F3 are, for example, infrared absorption filters. Coating for blocking YAG laser is applied on the object side surface of each plane parallel plate, and coating for blocking LD laser is applied on the image side surface of each plane parallel plate. Recently, there are cases where near-infrared fluorescent microscopy using a fluorescent agent is performed to evaluate blood flow or to identify a region to be ablated. For this purpose, a filter having a coating that blocks the wavelength of the excitation light and transmits the wavelength of the fluorescent light may be used instead of the infrared absorption filter.

FIGS. 3A to 3J are aberration diagrams of the objective optical system of example 1. In these aberration diagrams, FIY denotes the image height. DZY1 and DZY2 are longitudinal aberrations, and the other aberrations are lateral aberrations. In the aberration diagrams other than DZY1 and DZY2, the vertical axis represents the image height ratio. Therefore, in the aberration diagrams other than DZY1 and DZY2, the maximum value of the vertical axis is "the image height ratio=1". In the aberration diagrams of DZY1 and DZY2, the vertical axis represents the aperture ratio. The above description applies to the aberration diagrams for all the examples presented in the following.

FIG. 3A shows spherical aberration (DZY1, the image height FIY=0.0) in the normal observation state. FIG. 3B shows field curvature (FC) in the normal observation state. FIG. 3C shows chromatic aberration of magnification (CC) in the normal observation state. FIG. 3D shows distortion (DT) in the normal observation state. FIG. 3E shows coma (DZY2, FIY=1.032) in the normal observation state.

FIG. 3F shows spherical aberration (DZY1, the image height FIY=0.0) in the short-distance observation state. FIG. 3G shows field curvature (FC) in the short-distance observation state. FIG. 3H shows chromatic aberration of magnification (CC) in the short distance observation state. FIG. 3I shows distortion (DT) in the short-distance observation state. FIG. 3J shows coma (DZY2, FIY=1.032) in the short-distance observation state.

Example 2

An objective optical system 12 of example 2 will be described.

Figure 4:
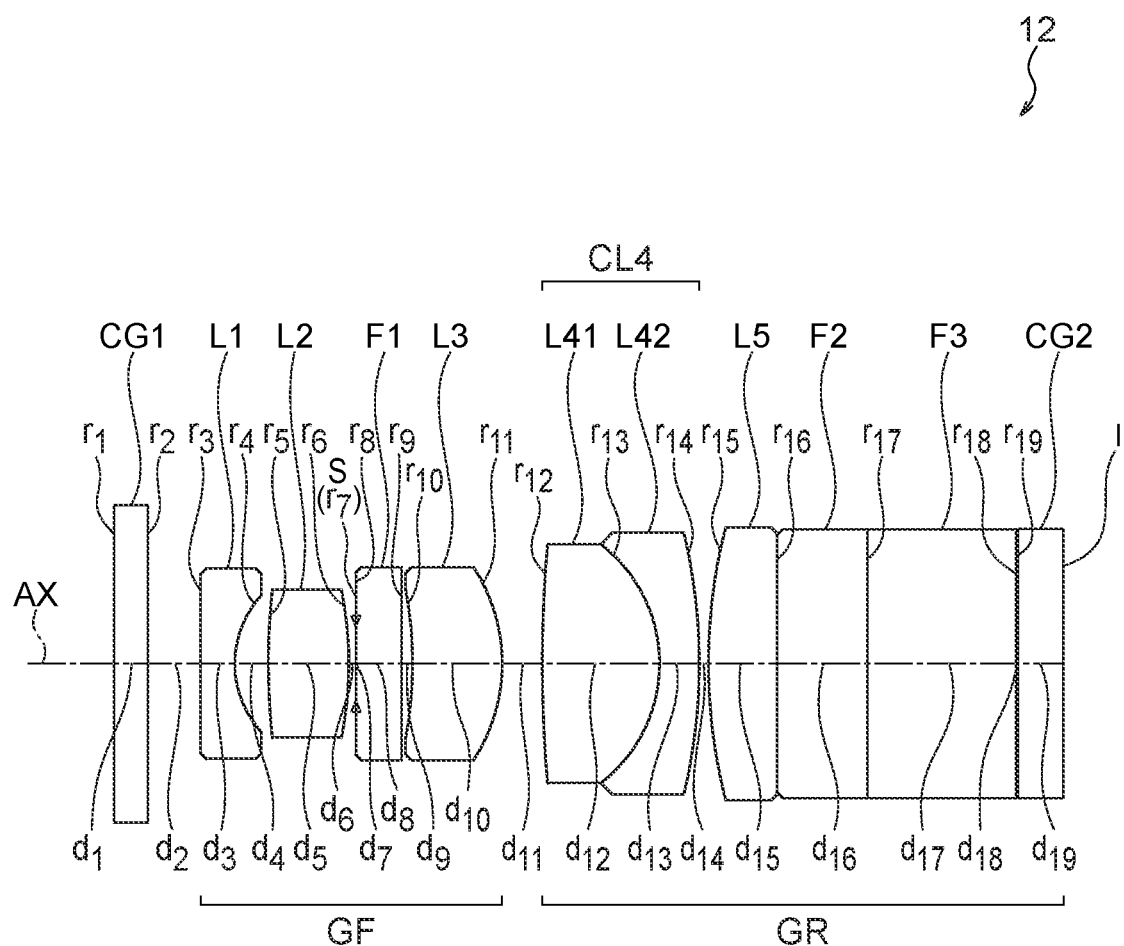
FIG. 4 is a cross sectional view of the lenses in an objective optical system of example 2.

FIG. 4 is a cross sectional view of the lenses in the objective optical system 12 of example 2 in a normal observation state.

The objective optical system 12 includes, in order from the object side to the image side, a positive front lens group GF and a positive rear lens group GR. The objective optical system 12 includes a cover glass CG1 disposed closest to the object.

The front lens group GF is moved along the optical axis AX to perform focusing, namely switching between the normal observation state and a short-distance observation state. What is denoted by I in FIG. 4 is the image plane or the image pickup surface.

The front lens group GF includes, in order from the object side, a negative planoconcave first lens L1 having a concave surface facing toward the image side, a positive biconvex second lens L2, an aperture stop S, a first plane parallel plate F1, and a positive meniscus third lens L3 having a convex surface facing toward the image side, as lenses having refractive power.

The rear lens group GR includes, in order from the object side, a positive biconvex lens L41, a negative meniscus lens L42 having a convex surface facing toward the image side, a positive planoconvex fifth lens L5 having a convex surface facing toward the object side, a second plane parallel plate F2, a third plane parallel plate F3, and a cover glass CG2. The positive lens L41 and the negative meniscus lens L42 are cemented together to constitute a positive cemented fourth lens CL4. The positive fifth lens L5, the second plane parallel plate F2, the third plane parallel plate F3, and the cover glass CG2 are cemented together. There is an adhesive layer between the third plane parallel plate F3 and the cover glass CG2.

The first to third plane parallel plates F1, F2, F3 are, for example, infrared absorption filters. Coating for blocking YAG laser is applied on the object side surface of each plane parallel plate, and coating for blocking LD laser is applied on the image side surface of each plane parallel plate. Recently, there are cases where near-infrared fluorescent microscopy using a fluorescent agent is performed to evaluate blood flow or to identify a region to be ablated. For this purpose, a filter having a coating that blocks the wavelength of the excitation light and transmits the wavelength of the fluorescent light may be used instead of the infrared absorption filter.

FIGS. 5A to 5J are aberration diagrams of the objective optical system of example 2. FIG. 5A shows spherical aberration (DZY1, the image height FIY=0.0) in the normal observation state. FIG. 5B shows field curvature (FC) in the normal observation state. FIG. 5C shows chromatic aberration of magnification (CC) in the normal observation state. FIG. 5D shows distortion (DT) in the normal observation state. FIG. 5E shows coma (DZY2, FIY=1.032) in the normal observation state.

FIG. 5F shows spherical aberration (DZY1, the image height FIY=0.0) in the short-distance observation state. FIG. 5G shows field curvature (FC) in the short-distance observation state. FIG. 5H shows chromatic aberration of magnification (CC) in the short distance observation state. FIG. 5I shows distortion (DT) in the short-distance observation state. FIG. 5J shows coma (DZY2, FIY=1.032) in the short-distance observation state.

Example 3

An objective optical system 13 of example 3 will be described.

Figure 6:
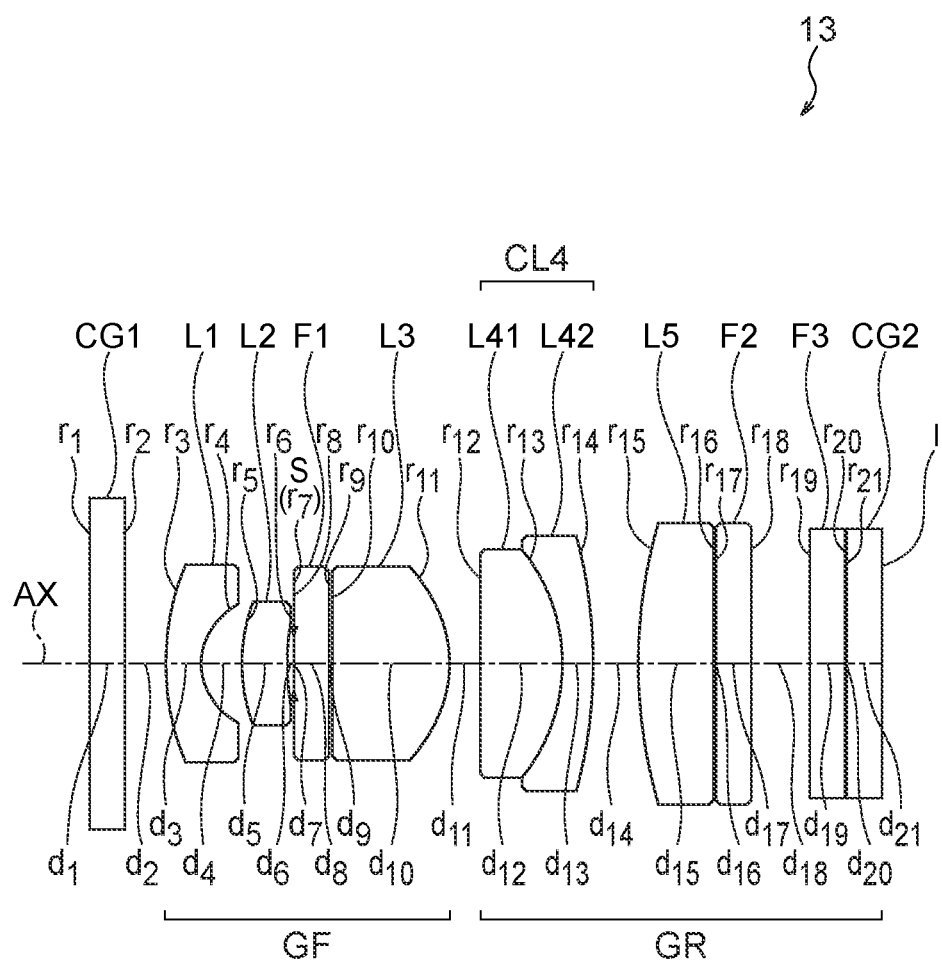
FIG. 6 is a cross sectional view of the lenses in an objective optical system of example 3.

FIG. 6 is a cross sectional view of the lenses in the objective optical system 13 of example 3 in a normal observation state.

The objective optical system 13 includes, in order from the object side to the image side, a positive front lens group GF and a positive rear lens group GR. The objective optical system 13 includes a cover glass CG1 disposed closest to the object.

The front lens group GF is moved along the optical axis AX to perform focusing, namely switching between the normal observation state and a short-distance observation state. What is denoted by I in FIG. 6 is the image plane or the image pickup surface.

The front lens group GF includes, in order from the object side, a negative meniscus first lens L1 having a convex surface facing toward the object side, a positive meniscus second lens L2 having a convex surface facing toward the object side, an aperture stop S, a first plane parallel plate F1, and a positive planoconvex third lens L3 having a convex surface facing toward the image side, as lenses having refractive power.

The rear lens group GR includes, in order from the object side, a positive planoconvex lens L41 having a convex surface facing toward the image side, a negative meniscus lens L42 having a convex surface facing toward the image side, a positive planoconvex fifth lens L5 having a convex surface facing toward the object side, a second plane parallel plate F2, a third plane parallel plate F3, and a cover glass CG2. The positive lens L41 and the negative meniscus lens L42 are cemented together to constitute a positive cemented fourth lens CL4. The third plane parallel plate F3 and the cover glass CG2 are cemented together. There is an adhesive layer between the third plane parallel plate F3 and the cover glass CG2.

There are three aspheric surfaces in the objective optical system 13, which are both surfaces of the negative meniscus first lens L1 and the image side surfaces of the positive third lens L3.

The first to third plane parallel plates F1, F2, F3 are, for example, infrared absorption filters. Coating for blocking YAG laser is applied on the object side surface of each plane parallel plate, and coating for blocking LD laser is applied on the image side surface of each plane parallel plate. Recently, there are cases where near-infrared fluorescent microscopy using a fluorescent agent is performed to evaluate blood flow or to identify a region to be ablated. For this purpose, a filter having a coating that blocks the wavelength of the excitation light and transmits the wavelength of the fluorescent light may be used instead of the infrared absorption filter.

FIGS. 7A to 7J are aberration diagrams of the objective optical system of example 3. FIG. 7A shows spherical aberration (DZY1, the image height FIY=0.0) in the normal observation state. FIG. 7B shows field curvature (FC) in the normal observation state. FIG. 7C shows chromatic aberration of magnification (CC) in the normal observation state. FIG. 7D shows distortion (DT) in the normal observation state. FIG. 7E shows coma (DZY2, FIY=1.032) in the normal observation state.

FIG. 7F shows spherical aberration (DZY1, the image height FIY=0.0) in the short-distance observation state. FIG. 7G shows field curvature (FC) in the short-distance observation state. FIG. 7H shows chromatic aberration of magnification (CC) in the short distance observation state. FIG. 7I shows distortion (DT) in the short-distance observation state. FIG. 7J shows coma (DZY2, FIY=1.032) in the short-distance observation state.

Example 4

An objective optical system 14 of example 4 will be described.

Figure 8:
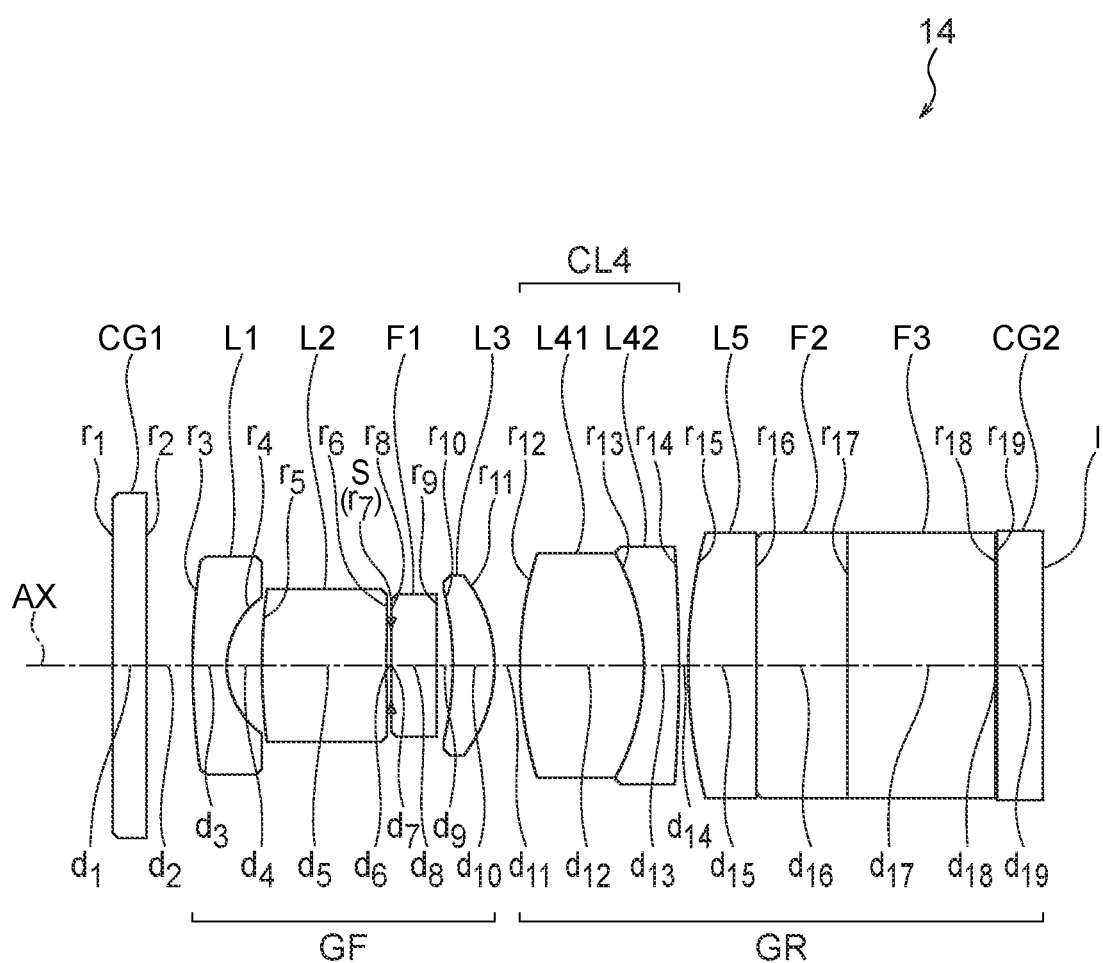
FIG. 8 is a cross sectional view of the lenses in an objective optical system of example 4.

FIG. 8 is a cross sectional view of the lenses in the objective optical system 14 of example 4 in a normal observation state.

The objective optical system 14 includes, in order from the object side to the image side, a positive front lens group GF and a positive rear lens group GR. The objective optical system 14 includes a cover glass CG1 disposed closest to the object.

The front lens group GF is moved along the optical axis AX to perform focusing, namely switching between the normal observation state and a short-distance observation state. What is denoted by I in FIG. 8 is the image plane or the image pickup surface.

The front lens group GF includes, in order from the object side, a negative meniscus first lens L1 having a convex surface facing toward the object side, a positive meniscus second lens L2 having a convex surface facing toward the object side, an aperture stop S, a first plane parallel plate F1, and a positive meniscus third lens L3 having a convex surface facing toward the image side, as lenses having refractive power.

The rear lens group GR includes, in order from the object side, a positive biconvex lens L41, a negative meniscus lens L42 having a convex surface facing toward the image side, a positive planoconvex fifth lens L5 having a convex surface facing toward the object side, a second plane parallel plate F2, a third plane parallel plate F3, and a cover glass CG2. The positive lens L41 and the negative meniscus lens L42 are cemented together to constitute a positive cemented fourth lens CL4. The positive fifth lens L5, the second plane parallel plate F2, the third plane parallel plate F3, and the cover glass CG2 are cemented together. There is an adhesive layer between the third plane parallel plate F3 and the cover glass CG2.

The first to third plane parallel plates F1, F2, F3 are, for example, infrared absorption filters. Coating for blocking YAG laser is applied on the object side surface of each plane parallel plate, and coating for blocking LD laser is applied on the image side surface of each plane parallel plate. Recently, there are cases where near-infrared fluorescent microscopy using a fluorescent agent is performed to evaluate blood flow or to identify a region to be ablated. For this purpose, a filter having a coating that blocks the wavelength of the excitation light and transmits the wavelength of the fluorescent light may be used instead of the infrared absorption filter.

FIGS. 9A to 9J are aberration diagrams of the objective optical system of example 4. FIG. 9A shows spherical aberration (DZY1, the image height FIY=0.0) in the normal observation state. FIG. 9B shows field curvature (FC) in the normal observation state. FIG. 9C shows chromatic aberration of magnification (CC) in the normal observation state. FIG. 9D shows distortion (DT) in the normal observation state. FIG. 9E shows coma (DZY2, FIY=1.032) in the normal observation state.

FIG. 9F shows spherical aberration (DZY1, the image height FIY=0.0) in the short-distance observation state. FIG. 9G shows field curvature (FC) in the short-distance observation state. FIG. 9H shows chromatic aberration of magnification (CC) in the short distance observation state. FIG. 9I shows distortion (DT) in the short-distance observation state. FIG. 9J shows coma (DZY2, FIY=1.032) in the short-distance observation state.

Example 5

An objective optical system 15 of example 5 will be described.

Figure 10:
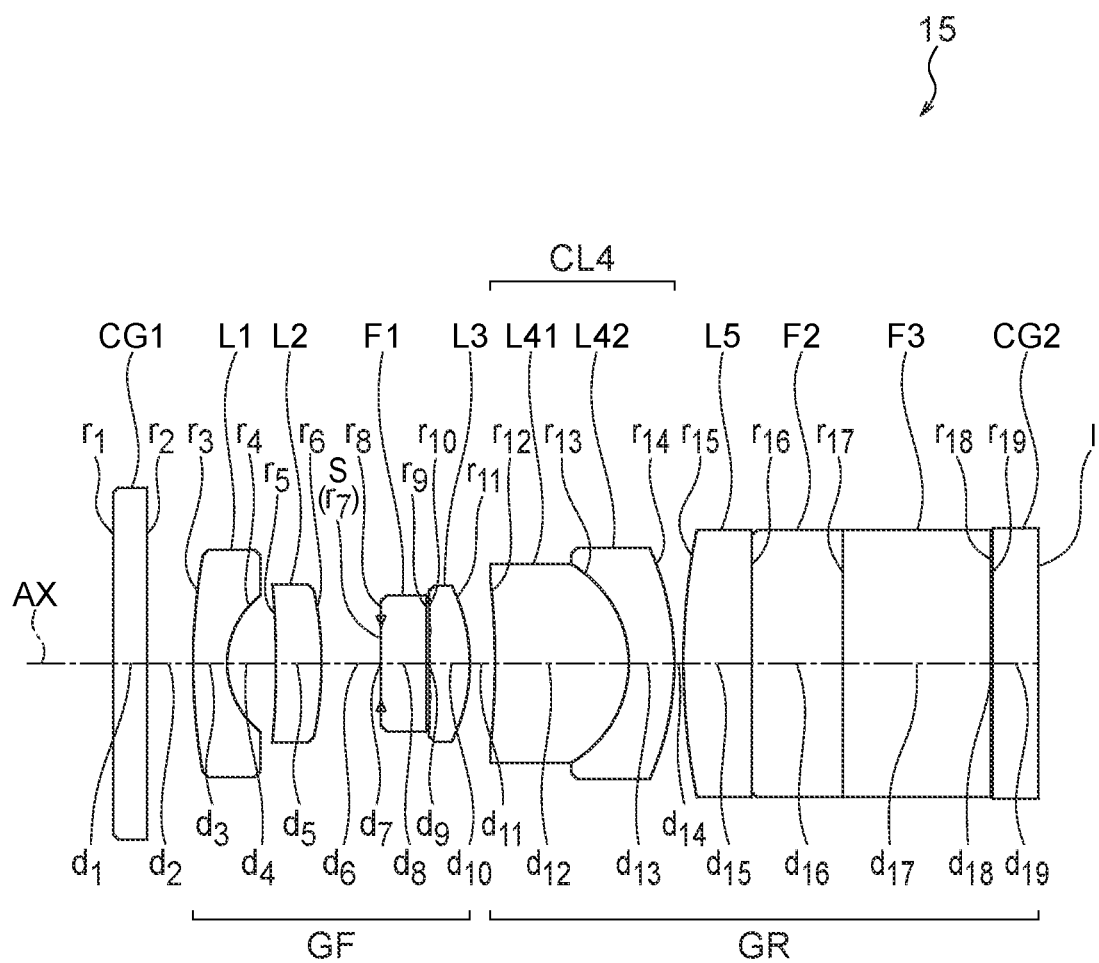
FIG. 10 is a cross sectional view of the lenses in an objective optical system of example 5.

FIG. 10 is a cross sectional view of the lenses in the objective optical system 15 of example 5 in a normal observation state.

The objective optical system 15 includes, in order from the object side to the image side, a positive front lens group GF and a positive rear lens group GR. The objective optical system 15 includes a cover glass CG1 disposed closest to the object.

The front lens group GF is moved along the optical axis AX to perform focusing, namely switching between the normal observation state and a short-distance observation state. What is denoted by I in FIG. 10 is the image plane or the image pickup surface.

The positive front lens group GF includes, in order from the object side, a negative meniscus first lens L1 having a convex surface facing toward the object side, a positive meniscus second lens L2 having a convex surface facing toward the image side, an aperture stop S, a first plane parallel plate F1, and a positive meniscus third lens L3 having a convex surface facing toward the image side, as lenses having refractive power.

The positive rear lens group GR includes, in order from the object side, a positive meniscus lens L41 having a convex surface facing toward the image side, a negative meniscus lens L42 having a convex surface facing toward the image side, a positive planoconvex fifth lens L5 having a convex surface facing toward the object side, a second plane parallel plate F2, a third plane parallel plate F3, and a cover glass CG2. The positive meniscus lens L41 and the negative meniscus lens L42 are cemented together to constitute a positive cemented fourth lens CL4. The positive fifth lens L5, the second plane parallel plate F2, the third plane parallel plate F3, and the cover glass CG2 are cemented together. There is an adhesive layer between the third plane parallel plate F3 and the cover glass CG2.

The first to third plane parallel plates F1, F2, F3 are, for example, infrared absorption filters. Coating for blocking YAG laser is applied on the object side surface of each plane parallel plate, and coating for blocking LD laser is applied on the image side surface of each plane parallel plate. Recently, there are cases where near-infrared fluorescent microscopy using a fluorescent agent is performed to evaluate blood flow or to identify a region to be ablated. For this purpose, a filter having a coating that blocks the wavelength of the excitation light and transmits the wavelength of the fluorescent light may be used instead of the infrared absorption filter.

FIGS. 11A to 11J are aberration diagrams of the objective optical system of example 5. FIG. 11A shows spherical aberration (DZY1, the image height FIY=0.0) in the normal observation state. FIG. 11B shows field curvature (FC) in the normal observation state. FIG. 11C shows chromatic aberration of magnification (CC) in the normal observation state. FIG. 11D shows distortion (DT) in the normal observation state. FIG. 11E shows coma (DZY2, FIY=1.032) in the normal observation state.

FIG. 11F shows spherical aberration (DZY1, the image height FIY=0.0) in the short-distance observation state. FIG. 11G shows field curvature (FC) in the short-distance observation state. FIG. 11H shows chromatic aberration of magnification (CC) in the short distance observation state. FIG. 11I shows distortion (DT) in the short-distance observation state. FIG. 11J shows coma (DZY2, FIY=1.032) in the short-distance observation state.

Example 6

An objective optical system 16 of example 6 will be described.

Figure 12:
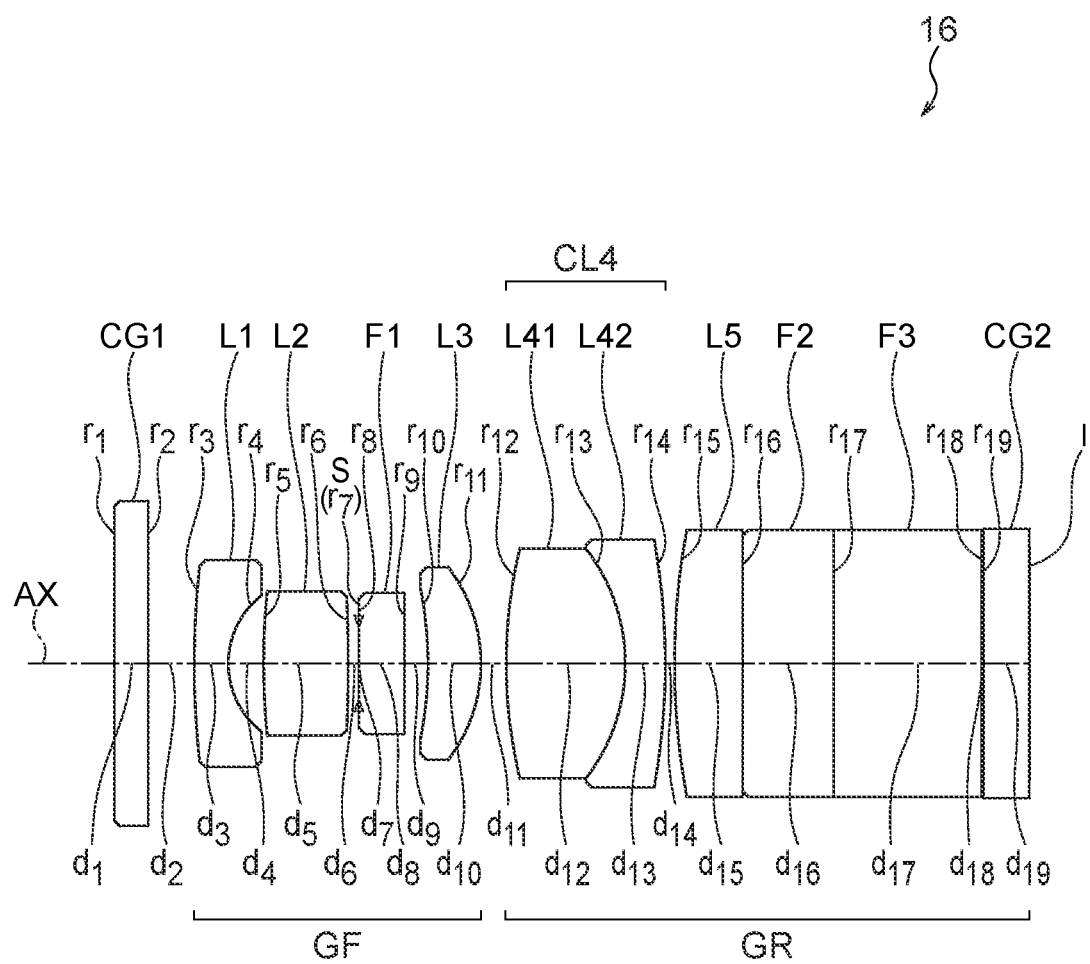
FIG. 12 is a cross sectional view of the lenses in an objective optical system of example 6.

FIG. 12 is a cross sectional view of the lenses in the objective optical system 16 of example 6 in a normal observation state.

The objective optical system 16 includes, in order from the object side to the image side, a positive front lens group GF and a positive rear lens group GR. The objective optical system 16 includes a cover glass CG1 disposed closest to the object.

The front lens group GF is moved along the optical axis AX to perform focusing, namely switching between the normal observation state and a short-distance observation state. What is denoted by I in FIG. 12 is the image plane or the image pickup surface.

The positive front lens group GF includes, in order from the object side, a negative meniscus first lens L1 having a convex surface facing toward the object side, a positive biconvex second lens L2, an aperture stop S, a first plane parallel plate F1, and a positive meniscus third lens L3 having a convex surface facing toward the image side, as lenses having refractive power.

The rear lens group GR includes, in order from the object side, a positive biconvex lens L41, a negative meniscus lens L42 having a convex surface facing toward the image side, a positive planoconvex fifth lens L5 having a convex surface facing toward the object side, a second plane parallel plate F2, a third plane parallel plate F3, and a cover glass CG2. The positive lens L41 and the negative meniscus lens L42 are cemented together to constitute a positive cemented fourth lens CL4. The positive fifth lens L5, the second plane parallel plate F2, the third plane parallel plate F3, and the cover glass CG2 are cemented together. There is an adhesive layer between the third plane parallel plate F3 and the cover glass CG2.

The first to third plane parallel plates F1, F2, F3 are, for example, infrared absorption filters. Coating for blocking YAG laser is applied on the object side surface of each plane parallel plate, and coating for blocking LD laser is applied on the image side surface of each plane parallel plate. Recently, there are cases where near-infrared fluorescent microscopy using a fluorescent agent is performed to evaluate blood flow or to identify a region to be ablated. For this purpose, a filter having a coating that blocks the wavelength of the excitation light and transmits the wavelength of the fluorescent light may be used instead of the infrared absorption filter.

FIGS. 13A to 13J are aberration diagrams of the objective optical system of example 6. FIG. 13A shows spherical aberration (DZY1, the image height FIY=0.0) in the normal observation state. FIG. 13B shows field curvature (FC) in the normal observation state. FIG. 13C shows chromatic aberration of magnification (CC) in the normal observation state. FIG. 13D shows distortion (DT) in the normal observation state. FIG. 13E shows coma (DZY2, FIY=1.032) in the normal observation state.

FIG. 13F shows spherical aberration (DZY1, the image height FIY=0.0) in the short-distance observation state. FIG. 13G shows field curvature (FC) in the short-distance observation state. FIG. 13H shows chromatic aberration of magnification (CC) in the short distance observation state. FIG. 13I shows distortion (DT) in the short-distance observation state. FIG. 13J shows coma (DZY2, FIY=1.032) in the short-distance observation state.

In the following, numerical data of the above-described examples will be given. In the surface data, r is the radius of curvature of each lens surface, d is the distance between adjacent lens surfaces, ne is the refractive index of each lens at e-line, vd is the Abbe number of each lens, and 2ω is the full angle of view. The term "stop" refers to the aperture stop in each example.

The aspherical shape is expressed by the following equation, where x is the optical axis with the light traveling in the positive direction and y is the direction orthogonal to the optical axis.

$$x=(y^2/r)/[1+\{1-(K+1)(y/r)^2\}^{1/2}]+A_4y^4+A_6y^6+A_8y^8+A_{10}y^{10}+A_{12}y^{12}$$

where r is the paraxial radius of curvature, K is the conic coefficient, and A4, A6, A8, A10, and A12 are respectively A4, A6, A8, A10, and A12 are the 4th, 6th, 8th, 10th, and 12th order aspheric coefficients, respectively. In the aspheric coefficients, "e-n" (n is an integer) indicates "$10^{-n}$".

Example 1

| Unit mm Surface data | | | | |
|---|---|---|---|---|
| Surface no. | r | d | ne | vd |
| Object plane | ∞ | 60 | 1 | |
| 1 | ∞ | 0.3 | 1.77066 | 71.79 |
| 2 | ∞ | Variable | 1 | |
| 3 | 46.1983 | 0.3 | 1.65222 | 33.79 |
| 4 | 0.7636 | 0.31 | 1 | |
| 5 | 9.5817 | 0.6162 | 1.97189 | 17.47 |
| 6 | −5.1681 | 0.1055 | 1 | |
| 7 (Stop) | ∞ | 0 | 1 | |
| 8 | ∞ | 0.4 | 1.523 | 66.5 |
| 9 | ∞ | 0.1784 | 1 | |
| 10 | −4.0598 | 0.5396 | 1.88815 | 40.76 |
| 11 | −1.4289 | Variable | 1 | |
| 12 | 6.2467 | 0.9704 | 1.65425 | 58.55 |
| 13 | −1.3928 | 0.4564 | 1.93429 | 18.9 |
| 14 | −4.7085 | 0.08 | 1 | |
| 15 | 6.8065 | 0.6 | 1.59143 | 61.14 |
| 16 | ∞ | 0.8 | 1.51825 | 64.14 |
| 17 | ∞ | 1.3 | 1.51825 | 64.14 |
| 18 | ∞ | 0.02 | 1.5119 | 64.05 |
| 19 | ∞ | 0.4 | 1.6135 | 50.49 |
| Image pickup surface | ∞ | 0 | | |

| Various data | | |
|---|---|---|
| | normal observation | short-distance observation |
| Object distance | 60 mm | 30 mm |
| Focal length | 1.429 | 1.445 |
| 2ω | 87.635 | 85.798 |
| d2 | 0.40331 | 0.30059 |
| d11 | 0.22167 | 0.32439 |

Example 2

| Unit mm Surface data | | | | |
|---|---|---|---|---|
| Surface no. | r | d | ne | vd |
| Object plane | ∞ | 60 | 1 | |
| 1 | ∞ | 0.3 | 1.77066 | 71.79 |
| 2 | ∞ | Variable | 1 | |
| 3 | ∞ | 0.3 | 1.79192 | 25.68 |
| 4 | 0.888 | 0.2945 | 1 | |
| 5 | 6.2538 | 0.7075 | 1.93429 | 18.9 |
| 6 | −3.2553 | 0.0622 | 1 | |
| 7 (Stop) | ∞ | 0 | 1 | |
| 8 | ∞ | 0.4 | 1.51825 | 64.14 |
| 9 | ∞ | 0.0979 | 1 | |
| 10 | −3.4961 | 0.7874 | 1.88815 | 40.76 |

-continued

| | | | | |
|---|---|---|---|---|
| 11 | −1.558 | Variable | 1 | |
| 12 | 12.1963 | 1.0302 | 1.69979 | 55.53 |
| 13 | −1.3299 | 0.35 | 1.93429 | 18.9 |
| 14 | −4.9364 | 0.08 | 1 | |
| 15 | 4.8295 | 0.6 | 1.59143 | 61.14 |
| 16 | ∞ | 0.8 | 1.51825 | 64.14 |
| 17 | ∞ | 1.3 | 1.51825 | 64.14 |
| 18 | ∞ | 0.02 | 1.5119 | 64.05 |
| 19 | ∞ | 0.4 | 1.6135 | 50.49 |
| Image pickup surface | ∞ | 0 | | |

Various data

| | normal observation | short-distance observation |
|---|---|---|
| Object distance | 60 mm | 30 mm |
| Focal length | 1.447 | 1.463 |
| 2ω | 86.465 | 84.659 |
| d2 | 0.46428 | 0.36632 |
| d11 | 0.35271 | 0.45067 |

Example 3

Unit mm
Surface data

| Surface no. | r | d | ne | νd |
|---|---|---|---|---|
| Object plane | ∞ | 70 | 1 | |
| 1 | ∞ | 0.4 | 1.77067 | 72.24 |
| 2 | ∞ | Variable | 1 | |
| 3* | 3.274 | 0.4 | 1.59143 | 61.15 |
| 4* | 0.7051 | 0.4631 | 1 | |
| 5 | 2.0148 | 0.514 | 1.92336 | 31.6 |
| 6 | 2.8558 | 0.0748 | 1 | |
| 7 (Stop) | ∞ | 0 | 1 | |
| 8 | ∞ | 0.4 | 1.51825 | 64.14 |
| 9 | ∞ | 0.0357 | 1 | |
| 10 | ∞ | 1.3335 | 1.68084 | 54.89 |
| 11* | −1.4438 | Variable | 1 | |
| 12 | ∞ | 0.9315 | 1.71615 | 53.87 |
| 13 | −2.0626 | 0.35 | 1.93429 | 18.9 |
| 14 | −5.6045 | 0.5121 | 1 | |
| 15 | 5.7205 | 0.8552 | 1.59143 | 61.14 |
| 16 | ∞ | 0.03 | 1 | |
| 17 | ∞ | 0.4 | 1.51825 | 64.14 |
| 18 | ∞ | 0.6627 | 1 | |
| 19 | ∞ | 0.4 | 1.51825 | 64.14 |
| 20 | ∞ | 0.02 | 1.5119 | 64.09 |
| 21 | ∞ | 0.4 | 1.61349 | 50.47 |
| Image pickup surface | ∞ | 0 | | |

Aspherical surface data
3rd surface
k = 3.8508
A2 = 0.00E+00, A4 = 1.57E−02, A6 = −1.6576E−02,
A8 = 0.00E+00, A10 = 0.00E+00
4th surface
k = −0.3652
A2 = 0.00E+00, A4 = 5.92E−02, A6 = 1.1300E−01,
A8 = 0.00E+00, A10 = 0.00E+00
11th surface
k = −0.9439
A2 = 0.00E+00, A4 = −2.04E−02, A6 = 0.00E+00,
A8 = 0.00E+00, A10 = 0.00E+00

Various data
normal observation 70 mm
intermediate short-distance observation 40 mm
short-distance observation 28 mm

| | | | |
|---|---|---|---|
| Object distance | 70 mm | 40 mm | 28 mm |
| Focal length | 1.702 | 1.715 | 1.728 |
| 2ω | 86.305 | 85.456 | 84.626 |
| d2 | 0.4698 | 0.39946 | 0.32941 |
| d11 | 0.3495 | 0.41984 | 0.48989 |

Example 4

Unit mm
Surface data

| Surface no. | r | d | ne | νd |
|---|---|---|---|---|
| Object plane | ∞ | 60 | 1 | |
| 1 | ∞ | 0.3 | 1.77066 | 71.79 |
| 2 | ∞ | Variable | 1 | |
| 3 | 6.2715 | 0.3 | 1.65222 | 33.79 |
| 4 | 0.7359 | 0.31 | 1 | |
| 5 | 5.2249 | 1.0933 | 1.97189 | 17.47 |
| 6 | 126.9299 | 0.0444 | 1 | |
| 7 (Stop) | ∞ | 0 | 1 | |
| 8 | ∞ | 0.4 | 1.523 | 66.5 |
| 9 | ∞ | 0.1403 | 1 | |
| 10 | −2.7559 | 0.3665 | 1.88815 | 40.76 |
| 11 | −1.2847 | Variable | 1 | |
| 12 | 3.2689 | 1.0924 | 1.65425 | 58.55 |
| 13 | −2.0523 | 0.3066 | 1.93429 | 18.9 |
| 14 | −14.7929 | 0.08 | 1 | |
| 15 | 4.5632 | 0.6 | 1.59143 | 61.14 |
| 16 | ∞ | 0.8 | 1.51825 | 64.14 |
| 17 | ∞ | 1.3 | 1.51825 | 64.14 |
| 18 | ∞ | 0.02 | 1.5119 | 64.05 |
| 19 | ∞ | 0.4 | 1.6135 | 50.49 |
| Image pickup surface | ∞ | 0 | | |

Various data

| | normal observation | short-distance observation |
|---|---|---|
| Object distance | 60 mm | 30 mm |
| Focal length | 1.425 | 1.460 |
| 2ω | 87.006 | 84.422 |
| d2 | 0.40331 | 0.12596 |
| d11 | 0.22167 | 0.49902 |

Unit mm
Surface data

| Surface no. | r | d | ne | νd |
|---|---|---|---|---|
| Object plane | ∞ | 60 | 1 | |
| 1 | ∞ | 0.3 | 1.77066 | 71.79 |
| 2 | ∞ | Variable | 1 | |
| 3 | 5.3167 | 0.3 | 1.65222 | 33.79 |
| 4 | 0.7611 | 0.43 | 1 | |
| 5 | −7.7094 | 0.4 | 1.97189 | 17.47 |
| 6 | −3.0652 | 0.5227 | 1 | |
| 7 (Stop) | ∞ | 0 | 1 | |
| 8 | ∞ | 0.4 | 1.523 | 66.5 |
| 9 | ∞ | 0.03 | 1 | |
| 10 | −24.9434 | 0.35 | 1.88815 | 40.76 |
| 11 | −1.5629 | Variable | 1 | |
| 12 | −6.8273 | 1.1754 | 1.65425 | 58.55 |
| 13 | −1.0062 | 0.4 | 1.93429 | 18.9 |

-continued

| | | | | |
|---|---|---|---|---|
| 14 | −2.49 | 0.08 | 1 | |
| 15 | 5.9471 | 0.6 | 1.59143 | 61.14 |
| 16 | ∞ | 0.8 | 1.51825 | 64.14 |
| 17 | ∞ | 1.3 | 1.51825 | 64.14 |
| 18 | ∞ | 0.02 | 1.5119 | 64.05 |
| 19 | ∞ | 0.4 | 1.6135 | 50.49 |
| Image pickup surface | ∞ | 0 | | |

Various data

| | normal observation | short-distance observation |
|---|---|---|
| Object distance | 60 mm | 30 mm |
| Focal length | 1.416 | 1.425 |
| 2ω | 84.474 | 83.325 |
| d2 | 0.40331 | 0.35779 |
| d11 | 0.22167 | 0.26718 |

Example 6

Unit mm
Surface data

| Surface no. | r | d | ne | vd |
|---|---|---|---|---|
| Object plane | ∞ | 60 | 1 | |
| 1 | ∞ | 0.3 | 1.77066 | 71.79 |
| 2 | ∞ | Variable | 1 | |
| 3 | 7.7548 | 0.3 | 1.65222 | 33.79 |
| 4 | 0.7615 | 0.31 | 1 | |
| 5 | 6.2384 | 0.7436 | 1.97189 | 17.47 |
| 6 | −13.1702 | 0.0941 | 1 | |
| 7 (Stop) | ∞ | 0 | 1 | |
| 8 | ∞ | 0.4 | 1.523 | 66.5 |
| 9 | ∞ | 0.2063 | 1 | |
| 10 | −3.3842 | 0.4666 | 1.88815 | 40.76 |
| 11 | −1.3903 | Variable | 1 | |
| 12 | 4.346 | 1.0464 | 1.65425 | 58.55 |
| 13 | −1.6463 | 0.3519 | 1.93429 | 18.9 |
| 14 | −6.1583 | 0.08 | 1 | |
| 15 | 6.3656 | 0.6 | 1.59143 | 61.14 |
| 16 | ∞ | 0.8 | 1.51825 | 64.14 |
| 17 | ∞ | 1.3 | 1.51825 | 64.14 |
| 18 | ∞ | 0.02 | 1.5119 | 64.05 |
| 19 | ∞ | 0.4 | 1.6135 | 50.49 |
| Image pickup surface | ∞ | 0 | | |

Various data

| | normal observation | short-distance observation |
|---|---|---|
| Object distance | 60 mm | 30 mm |
| Focal length | 1.456 | 1.481 |
| 2ω | 84.720 | 82.517 |
| d2 | 0.40331 | 0.23603 |
| d11 | 0.22167 | 0.38895 |

Presented in the following is the values of the respective parameters and the values of the terms defined in conditional expressions in the above-described examples.

Parameters
(a) FL: the focal length of the entire system
(b) Ff: the focal length of the front lens group
(c) β: the imaging magnification of the front lens group in the normal observation state
(d) γ: the imaging magnification of the rear lens group in the normal observation state
(e) 2ω: the diagonal angle of view
(f) r1i: the curvature radius of the surface of the negative first lens that faces toward the imager
(g) r3i: the curvature radius of the surface of the positive third lens that faces toward the imager
(h) Ff: the focal length of the front lens group
(i) r4c: the curvature radius of the cemented surface of the fourth lens
(j) r5o: the curvature radius of the object side surface of the positive fifth lens
(k) Fr: the focal length of the rear lens group Conditional Expressions $$Fl/Ff \tag{1}$$

$$(r1i \times r3i)/Ff^2 \tag{2}$$

$$(r4c \times r5o)/Fr^2 \tag{3}$$

$$(1-\beta^2) \times \gamma^2 \tag{4}$$

| | Example 1 | | Example 2 | |
|---|---|---|---|---|
| | Normal Far point 60 mm | Short distance Near Point 30 mm | Normal Far point 60 mm | Short distance Near Point 30 mm |
| (a) | 1.429 | 1.445 | 1.447 | 1.463 |
| (b) | 2.486 | 2.486 | 2.432 | 2.432 |
| (c) | −0.041 | −0.083 | −0.040 | −0.081 |
| (d) | 0.5684 | 0.5684 | 0.5882 | 0.5882 |
| (e) | 87.635 | 85.798 | 86.465 | 84.659 |
| (f) | 0.764 | | 0.888 | |
| (g) | −1.429 | | −1.558 | |
| (h) | 2.486 | | 2.432 | |
| (i) | −1.393 | | −1.330 | |
| (j) | 6.807 | | 4.830 | |
| (k) | 5.299 | | 5.162 | |
| (1) | 0.575 | 0.581 | 0.595 | 0.602 |
| (2) | −0.177 | | −0.234 | |
| (3) | −0.338 | | −0.241 | |
| (4) | 0.323 | 0.321 | 0.345 | 0.344 |

| | Example 3 | | Example 4 | |
|---|---|---|---|---|
| | Normal Far point 70 mm | Short distance Near Point 28 mm | Normal Far point 60 mm | Short distance Near Point 30 mm |
| (a) | 1.702 | 1.728 | 1.425 | 1.460 |
| (b) | 2.587 | 2.587 | 3.993 | 3.993 |
| (c) | −0.037 | −0.091 | −0.067 | −0.137 |
| (d) | 0.6511 | 0.6680 | 0.3486 | 0.3486 |
| (e) | 86.305 | 84.626 | 87.006 | 84.222 |
| (f) | 0.705 | | 0.736 | |
| (g) | −1.444 | | −1.285 | |
| (h) | 2.587 | | 3.993 | |
| (i) | −2.0626 | | −2.052 | |
| (j) | 5.7205 | | 4.563 | |
| (k) | 6.020 | | 4.080 | |
| (1) | 0.658 | 0.663 | 0.357 | 0.366 |
| (2) | −0.152 | | −0.059 | |
| (3) | −0.326 | | −0.563 | |
| (4) | 0.423 | 0.420 | 0.121 | 0.119 |

| | Example 5 | | Example 6 | |
|---|---|---|---|---|
| | Normal Far point 60 mm | Short distance Near Point 30 mm | Normal Far point 60 mm | Short distance Near Point 30 mm |
| (a) | 1.416 | 1.425 | 1.456 | 1.481 |
| (b) | 1.678 | 1.678 | 3.143 | 3.143 |
| (c) | −0.028 | −0.055 | −0.052 | −0.106 |
| (d) | 0.8390 | 0.8390 | 0.4558 | 0.4558 |
| (e) | 84.474 | 83.325 | 84.720 | 82.517 |
| (f) | 0.761 | | 0.762 | |
| (g) | −1.563 | | −1.390 | |
| (h) | 1.678 | | 3.143 | |
| (i) | −1.006 | | −1.646 | |

-continued

|     |        |       |        |       |
| --- | ------ | ----- | ------ | ----- |
| (j) | 5.947  |       | 6.366  |       |
| (k) | 6.572  |       | 4.606  |       |
| (1) | 0.844  | 0.849 | 0.463  | 0.471 |
| (2) | −0.422 |       | −0.107 |       |
| (3) | −0.139 |       | −0.494 |       |
| (4) | 0.703  | 0.702 | 0.207  | 0.205 |

Two or more features of the above-described objective optical systems may be employed in combination. To provide an objective optical system having good performance, it is preferred to employ two or more features. Features may be employed in any preferable combination. In the conditional expressions that apply further limitation to the numerical ranges of preceding conditional expressions, the further limitation may be applied to only one of the upper and lower limit values.

While various embodiments of the present invention have been described, the present invention is not limited only to the embodiments. Other embodiments that employ features of the above-described embodiments in combination will also fall within the scope of the present invention, so long as they do not depart from the essence of the present invention.

As above, the present invention can suitably be applied to objective optical systems, image pickup apparatuses, and endoscopes that are required to be short in overall length and The present invention can provide an objective optical system, an image pickup apparatus, and an endoscope that are short in overall length and simple in structure and have a focusing function.

What is claimed is:

1. An objective optical system comprising, in order from the object side to the image side:
    a positive front lens group; and
    a positive rear lens group,
    wherein focusing is performed by moving the front lens group along the optical axis,
    the front lens group includes, in order from the object side, a negative first lens, a positive second lens, an aperture stop, and a positive third lens, as lenses having refractive power,
    the rear lens group includes, in order from the object side, a positive cemented fourth lens and a positive fifth lens having a convex surface facing toward the object, and
    the objective optical system satisfies the following conditional expression (1):

$$0.35 < FL/Ff < 0.85 \quad (1)$$

where Ff is the focal length of the front lens group, and FL is the focal length of the entire objective optical system in a normal observation state.

2. An objective optical system according to claim 1, wherein the objective optical system satisfies the following conditional expression (2):

$$-0.43 < (r1i \times r3i)/Ff^2 < -0.05 \quad (2)$$

where r1i is the curvature radius of the image side surface of the negative first lens, r3i is the curvature radius of the image side surface of the positive third lens, and Ff is the focal length of the front lens group.

3. An objective optical system according to claim 1, wherein the objective optical system satisfies the following conditional expression (3):

$$-0.57 < (r4c \times r5o)/Fr^2 < -0.13 \quad (3)$$

where r4c is the curvature radius of the cemented surface of the positive cemented fourth lens, r5o is the curvature radius of the object side surface of the positive fifth lens, and Fr is the focal length of the rear lens group.

4. An objective optical system according to claim 1, wherein the negative first lens is a negative bi-aspheric meniscus lens having a convex surface facing toward the object side, the positive second lens is a positive meniscus lens having a convex surface facing toward the object side, and the positive third lens is a positive lens whose image side surface is an aspheric surface.

5. An image pickup apparatus comprising:
    an objective optical system; and
    an imager,
    wherein and the objective optical system is an objective optical system according to claim 1.

6. An image pickup apparatus according to claim 5, wherein the following conditional expression (2) is satisfied:

$$-0.43 < (r1i \times r3i)/Ff^2 < -0.05 \quad (2)$$

where r1i is the curvature radius of the image side surface of the negative first lens, r3i is the curvature radius of the image side surface of the positive third lens, and Ff is the focal length of the front lens group.

7. An image pickup apparatus according to claim 5, wherein the following conditional expression (3) is satisfied:

$$-0.57 < (r4c \times r5o)/Fr^2 < -0.13 \quad (3)$$

where r4c is the curvature radius of the cemented surface of the positive cemented fourth lens, r5o is the curvature radius of the object side surface of the positive fifth lens, and Fr is the focal length of the rear lens group.

8. An image pickup apparatus according to claim 5, wherein the negative first lens is a negative bi-aspheric meniscus lens having a convex surface facing toward the object side, the positive second lens is a positive meniscus lens having a convex surface facing toward the object side, and the positive third lens is a positive lens whose image side surface is an aspheric surface.

9. An endoscope comprising:
    an objective optical system; and
    an imager,
    wherein the objective optical system is an objective optical system according to claim 1.

10. An endoscope according to claim 9, wherein the following conditional expression (2) is satisfied:

$$-0.43 < (r1i \times r3i)/Ff^2 < -0.05 \quad (2)$$

where r1i is the curvature radius of the image side surface of the negative first lens, r3i is the curvature radius of the image side surface of the positive third lens, and Ff is the focal length of the front lens group.

11. An endoscope according to claim 9, wherein the following conditional expression (3) is satisfied:

$$-0.57 < (r4c \times r5o)/Fr^2 < -0.13 \quad (3)$$

where r4c is the curvature radius of the cemented surface of the positive cemented fourth lens, r5o is the curvature radius of the object side surface of the positive fifth lens, and Fr is the focal length of the rear lens group.

12. An endoscope according to claim 9, wherein the negative first lens is a negative bi-aspheric meniscus lens having a convex surface facing toward the object side, the positive second lens is a positive meniscus lens having a convex surface facing toward the object side, and the positive third lens is a positive lens whose image side surface is an aspheric surface.

* * * * *